United States Patent
Salla et al.

(10) Patent No.: US 6,771,999 B2
(45) Date of Patent: Aug. 3, 2004

(54) DETERMINATION OF ARBITRARY CARDIAC PHASES USING NON-ELECTRICAL SIGNALS

(75) Inventors: Prathyusha K. Salla, Waukesha, WI (US); Gopal B. Avinash, New Berlin, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 61 days.

(21) Appl. No.: 10/065,961

(22) Filed: Dec. 4, 2002

(65) Prior Publication Data

US 2004/0111038 A1 Jun. 10, 2004

(51) Int. Cl.$^7$ ................................................ A61B 5/055
(52) U.S. Cl. .................................................... 600/413
(58) Field of Search ................................ 600/407–526

(56) References Cited

U.S. PATENT DOCUMENTS

| | | | |
|---|---|---|---|
| 4,712,560 A | 12/1987 | Schaefer et al. | 128/653 |
| 5,797,395 A | 8/1998 | Martin | 128/673 |
| 5,987,983 A | 11/1999 | Ariav et al. | 73/488 |
| 5,997,883 A | 12/1999 | Epstein et al. | 424/306 |
| 6,070,097 A | 5/2000 | Kreger et al. | 600/521 |
| 6,144,874 A | 11/2000 | Du | 600/413 |
| 6,243,437 B1 | 6/2001 | Hu et al. | 378/8 |
| 6,275,560 B1 | 8/2001 | Blake et al. | 378/8 |
| 6,434,215 B1 | 8/2002 | Cesmeli | 378/8 |

OTHER PUBLICATIONS

"Medical/ Biotechnological Field– Fields and Applications", Girad Systems– Fields and Applications, www.giradsystems.com, Oct. 30, 2002, 3 pages.
"Real–Time Position Management RPM", Varian Medical Systems, www.varian.com, Nov. 13, 2002, 3 pages.
"Respiration Movement Syncronization System", Anzai Medical Co., Ltd., www.anzai–med.co.jp, Nov. 13, 2002, 2 pages.

Primary Examiner—Scott M. Getzow
(74) Attorney, Agent, or Firm—Cantor Colburn LLP

(57) ABSTRACT

A method, storage medium, and system for selecting an optimal trigger point in a cardiac cycle includes providing an input signal including non-electrical cardiac related data, analyzing the input signal to detect candidate features, sorting through the candidate features to select optimal features, and selecting an optimal trigger point. A method, storage medium, and system of selecting an arbitrary cardiac phase for cardiac gating includes identifying a trigger point identifying onset of a systole or diastole phase on a signal, the trigger point existing at time t1, specifying a time δ t before the trigger point and extending from a time t0 to a time t1, wherein time t0 is earlier than time t1, and selecting a time interval T over which an image will be reconstructed, wherein the time interval T extends from time t0 to a time t2, wherein time t2 is later than time t0.

33 Claims, 11 Drawing Sheets

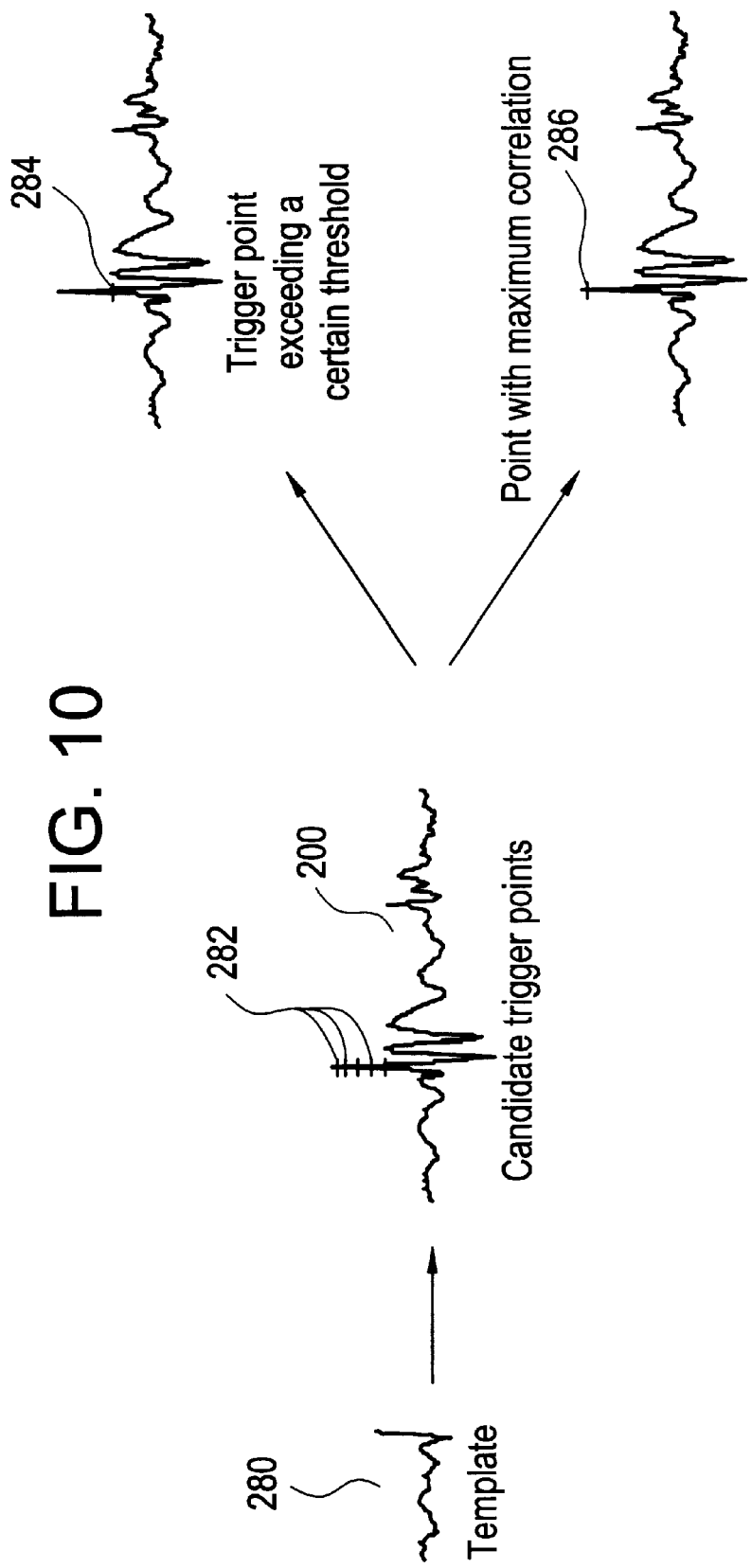

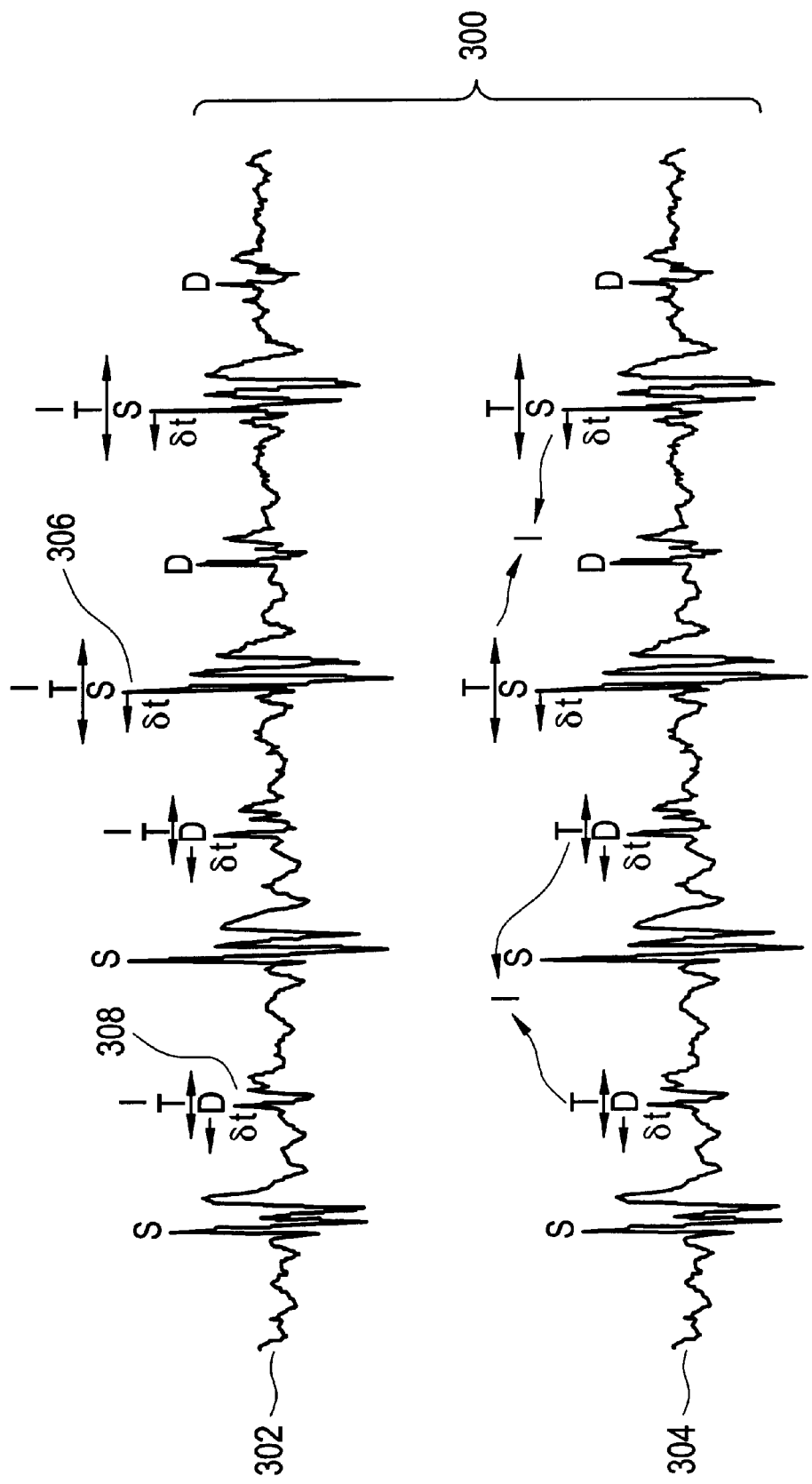

DETERMINATION OF ARBITRARY CARDIAC PHASES USING NON-ELECTRICAL SIGNALS

BACKGROUND OF THE INVENTION

This invention relates to gating for medical imaging, and more particularly, this invention relates to a method and system of selecting an arbitrary cardiac phase in physiological, non-electrical signals for cardiac gating.

In many applications, it is often desirable to obtain an image at a particular point in a variable cycle, such as a peak of the variable cycle, to analyze behavior at that peak. In the medical field, imaging systems are often used to obtain internal physiological information of a subject. For example, a medical imaging system may be used to obtain images of the bone structure, the brain, the heart, the lungs, and various other features of a subject. Medical imaging systems include magnetic resonance imaging (MRI) systems, computed tomography (CT) systems, x-ray systems, ultrasound systems, and various other imaging modalities.

Gating is essential for characterizing different attributes of a dynamic organ during imaging. The most common techniques of gating including cardiac, respiratory, and peripheral pulse gating have uses in numerous medical applications across diagnostic modalities including CT, MR, X-Ray, Ultrasound, and PET-CT.

Cardiac gating is an essential component of cardiac imaging while using imaging modalities such as CT, magnetic resonance (MR) to minimize motion related artifacts. Current cardiac imaging tools utilize simultaneously collected EKG data to tag CT projection data with cardiac phase information. Essentially, the R-wave of the EKG is used for this purpose. Heart functions are characterized by two distinct periods called systole and diastole. In systole, the heart-muscle is contracting the volume of the left ventricle to pump the contents out through the aortic valve. During the diastole, or diastolic period, the left ventricle is filling through the mitral valve. At the end of the systole, the left ventricle has its smallest volume since it has been contracted to pump blood out. The end of the diastole is the point at which the left ventricle has its largest volume since it is filled with blood ready to be pumped out. During the diastolic period the heart is relatively motion-free allowing images generated from data collected during this period to be clearer as a result of the limited movement.

FIG. 1 illustrates one cardiac cycle of an EKG signal waveform, including a systole condition, or period, and a diastole condition, or period, of the heart. The portions of the EKG signal labeled Q, R and S are referred to as the QRS complex, in which the R-feature, or R-wave, is the most prominent, highest amplitude, feature of the entire EKG signal. The cardiac cycle is typically defined as beginning with an R-wave and continuing until the occurrence of a next R-wave.

EKG gating selects times when a best image of the heart is available. An EKG machine is connected to a patient. A cardiac cycle period is determined, for example, as a time between R-peaks of the EKG. One of the common applications is to use an R-peak as a reference along with the determined cardiac cycle period, to acquire gated images during periods of a cardiac cycle for which the heart is nearly stationary, or during periods for which imaging is desired.

Turning now to FIG. 2, two of the commonly used approaches, shown collectively at 130, for determining the diastole and systole phases in a cardiac cycle using an EKG signal are shown. In waveform 132, the systolic 134 and diastolic 136 phases are centered at x % and y %, respectively in a cardiac cycle. In waveform 140, the systolic phase 142 is certain delay from the previous R-peak 146. Similarly, the systolic phase 144 is certain delay from the previous R-peak 148. The diastolic phase 152 is certain advance from the next R-peak 148, and similarly, the diastolic phase 154 is certain advance from the next R-peak 150. These approaches 130 are based on an assumption that the cardiac phases would occur at a certain time interval during the cardiac cycle. This assumption may not necessarily be accurate for every cardiac cycle and for every individual in a population.

Once the location for the systolic and diastolic phases are made or estimated using one of the approaches described above in FIG. 2, image reconstruction may be performed. FIG. 3 shows half scan and multi-sector image reconstruction where "I" represents the image reconstructed from a single cycle and two consecutive cycles respectively. In waveform 122 of EKG waveforms 120, projections 126 from a single cardiac cycle, also known as half-scan reconstruction, for a dataset for reconstruction. In waveform 124, subsets 128 of projections 126 from multiple cardiac cycles are blended, also known as sector based reconstruction, to form a complete dataset for reconstruction.

BRIEF SUMMARY OF THE INVENTION

The above discussed and other drawbacks and deficiencies are overcome or alleviated by a method of selecting an optimal trigger point in a cardiac cycle, the method including providing an input signal including non-electrical cardiac related data, analyzing the input signal to detect candidate features, sorting through the candidate features to select optimal features, and selecting an optimal trigger point.

In another embodiment, a method of selecting an arbitrary cardiac phase for cardiac gating includes identifying a trigger point identifying onset of a systole or diastole phase on a signal, the trigger point existing at time t1, specifying a time δ t before the trigger point and extending from a time t0 to a time t1, wherein time t0 is earlier than time t1, and selecting a time interval T over which an image will be reconstructed, wherein the time interval T extends from time t0 to a time t2, wherein time t2 is later than time t0.

In another embodiment, a method of image reconstruction using cardiac gating includes providing a signal indicative of a plurality of consecutive cardiac cycles, for each cardiac cycle, the method further including identifying a trigger point identifying onset of a systole or diastole phase, the trigger point existing at time t1, specifying a time δ t before the trigger point and extending from a time t0 to a time t1, wherein time t0 is earlier than time t1, selecting a time interval T over which an image will be reconstructed, wherein the time interval T extends from time t0 to a time t2, wherein time t2 is later than time t0, and reconstructing an image over at least one time interval T.

In another embodiment, a storage medium is encoded with a machine readable computer program code, the code including instructions for causing a computer to implement a method for selecting an optimal trigger point in a cardiac cycle, the method including providing an input signal including non-electrical cardiac related data, analyzing the input signal to detect candidate features, sorting through the candidate features to select optimal features, and selecting an optimal trigger point.

In another embodiment, a storage medium is encoded with a machine readable computer program code, the code including instructions for causing a computer to implement a method for selecting an arbitrary cardiac phase for cardiac gating, the method including identifying a trigger point identifying onset of a systole or diastole phase on a signal, the trigger point existing at time t1, specifying a time δ t before the trigger point and extending from a time t0 to a time t1, wherein time t0 is earlier than time t1, and selecting a time interval T over which an image will be reconstructed, wherein the time interval T extends from time t0 to a time t2, wherein time t2 is later than time t0.

In another embodiment, a system for selecting an optimal trigger point in a cardiac cycle includes a non-electrical sensor sensing mechanical vibrations of the heart, a processing circuit coupled to the mechanical sensor, the processing circuit processing a signal sent by the mechanical sensor, analyzing the signal to detect candidate features, sorting through the candidate features to select optimal features, and selecting an optimal trigger point.

In another embodiment, a system for image reconstruction using cardiac gating includes a non-electrical sensor sensing mechanical vibrations of the heart, a processing circuit coupled to the mechanical sensor, the processing circuit processing a signal sent by the mechanical sensor, identifying a trigger point identifying onset of a systole or diastole phase on the signal, the trigger point existing at time t1, specifying a time δ before the trigger point and extending from a time t0 to a time t1, wherein time t0 is earlier than time t1, and selecting a time interval T over which an image will be reconstructed, wherein the time interval T extends from time t0 to a time t2, wherein time t2 is later than time t0.

The above discussed and other features and advantages of the present invention will be appreciated and understood by those skilled in the art from the following detailed description and drawings.

BRIEF DESCRIPTION OF THE DRAWINGS

FIG. 10 shows an example of the template matching method of FIG. 9 applied to an acceleration signal for selecting trigger points; and, FIG. 11 shows waveforms where images are reconstructed over an interval 'T' determined by the time before the onset of different phases.

DETAILED DESCRIPTION OF THE INVENTION

In this method and system, the mechanical motion of the heart is used to reliably detect the cardiac phases and also provide the capability of selecting an arbitrary phase for reconstructing images.

For a method based on mechanical motion to be applicable for cardiac gating, the following three conditions have to apply: 1) causality: the gating signal needs to occur just before the cardiac displacement occurs (i.e., need to have capability to "look forward in time"); 2) specificity: the gating signal must be derived from an event that is cardiac in origin; and, 3) signature: the gating signal must be reliably obtained using a signature analysis approach. Thus, for any biological signal from a transducer to have biological relevance, conditions such as causality, specificity, and signature/pattern analysis need to be satisfied. Methods and systems for satisfying these conditions for cardiac, respiratory, and peripheral pulse gating are disclosed in U.S. patent application Ser. No. 10/065,960, filed concurrently herewith, and incorporated by reference in its entirety.

In this method and system described below, the cardiac signature/pattern analysis aspect of the non-electrical signals is described. This method and system applies to non-electrical signals such as peripheral pulse, phonocardiogram, and displacement/acceleration signals using various non-electrical sensors including displacement, acceleration, pressure, ultrasonic, force, optical, piezoelectric, resistive, inductive and capacitive transducers.

Figure 4:
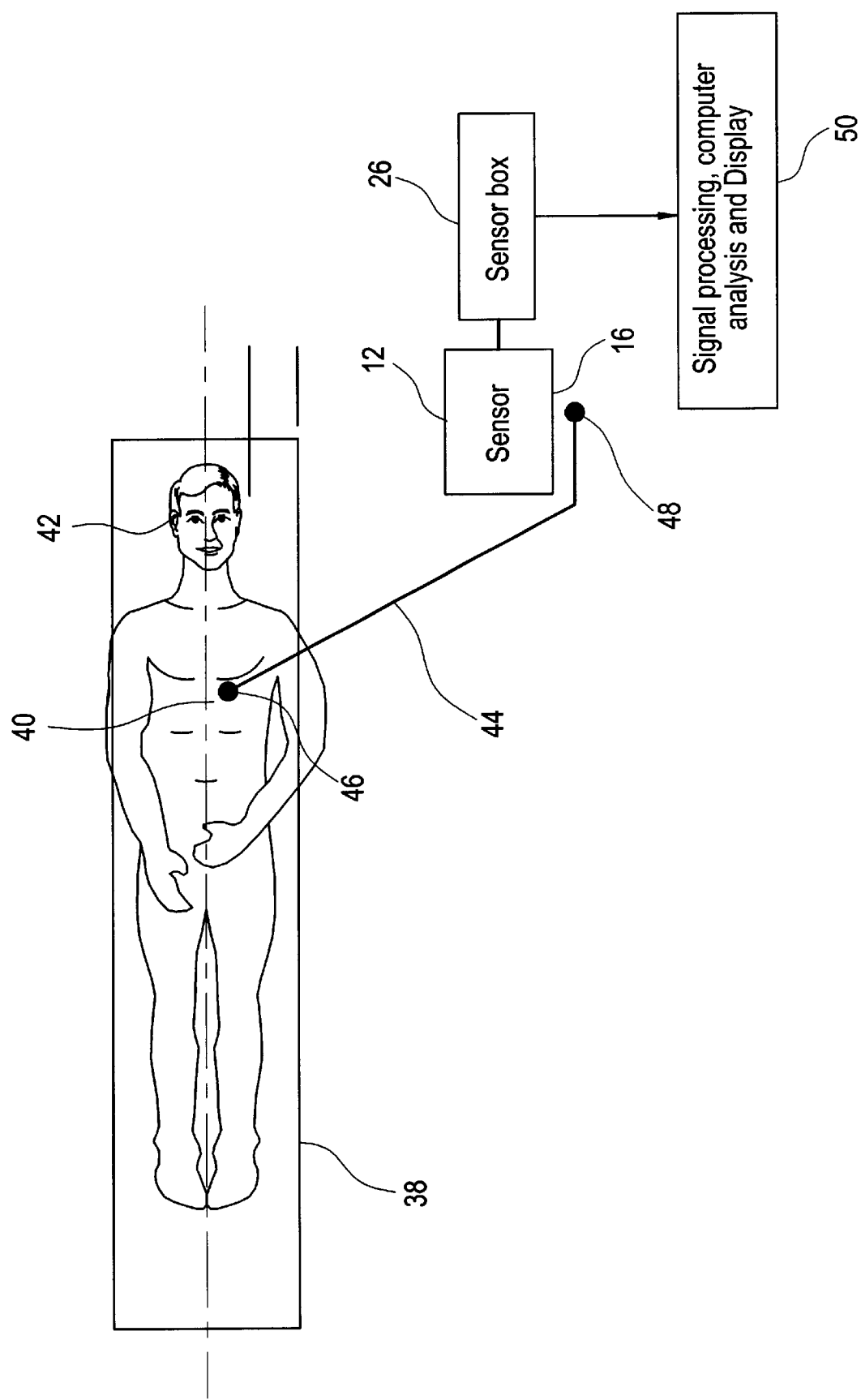
FIG. 4 shows a diagram of a sensor assembly arranged relative to a patient.

A non-electrical sensor such as a mechanical (acceleration) sensor is used as an example in this method and system unless otherwise specified, although any other suitable type of non-electrical sensor may be incorporated. In order to improve specificity, a sensor assembly, such as an accelerometer or any of the other non-electrical sensors described above, may be placed directly on the chest wall 40 in front of the heart of a patient 42 who is preferably supine on a table 38 as shown in FIG. 4. Alternatively, if the sensor 12 is interfering with imaging, for which gating is performed in the first place, the sensor 12 may be removed from the imaging field of view through the use of a fluid filled, non metallic, non conducting tube 44. The tube 44 may have a flat end 46, which is stuck, adhered, or otherwise secured to the patient 42, and the other end 48 may be placed under the sensor 12, below bottom surface 16. With this arrangement, the vibrations specific to the heart are conducted away to the sensor 12 which is located outside the imaging field of view. The cardiac vibrations from the patient are transferred using the fluid filled conduction device 44 to the sensor 12. If the sensor 12 is an accelerometer, then acceleration is recorded by the sensor box 26 and sent to signal processing, computer analysis and display 50. Although the incorporation of tube 44 introduces some conduction delay, it is not expected to significantly affect the causality of the signal. Alternate methods for removing the sensor 12 away from the imaging field of view are also usable within this method, as well as placing the sensor 12 directly on the chest 40 of the patient 42 when such a placement does not interfere with imaging.

Figure 5:
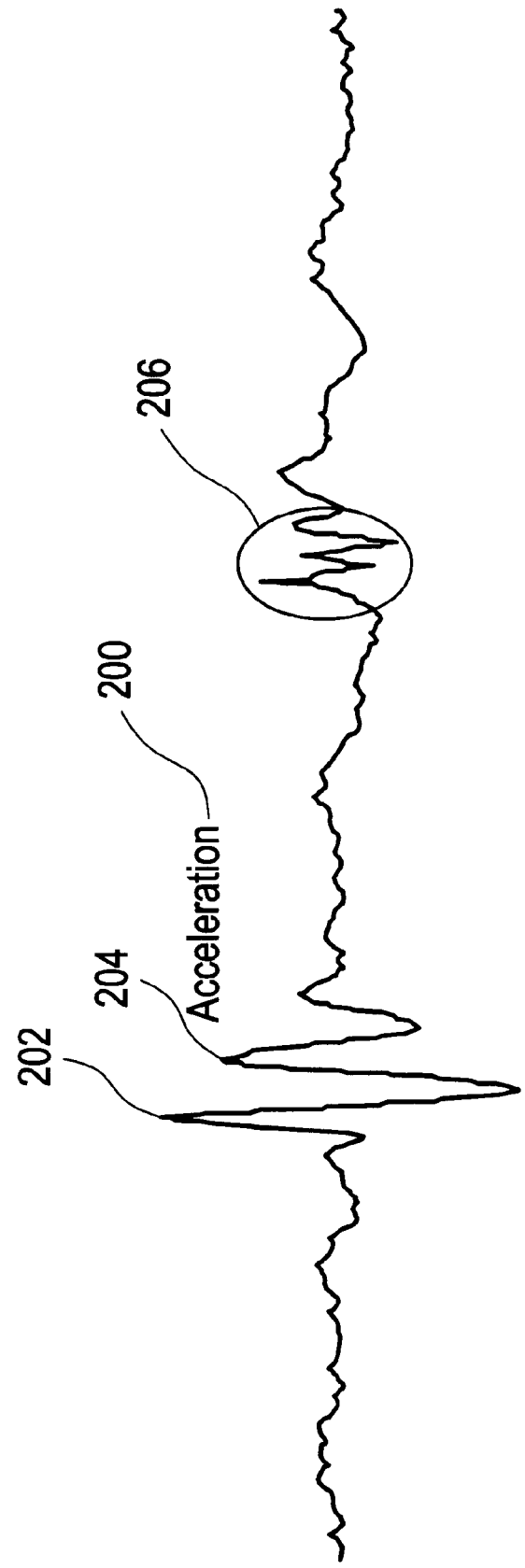
FIG. 5 shows a diagram of an acceleration signal of a cardiac cycle.

When a non-electrical sensor such as an accelerometer is placed in contact with a moving body, for instance, the front chest wall 40 as-shown in FIG. 4, movement of the front chest wall 40 representing the mechanical motion of the heart is detected. FIG. 5 shows the acceleration of the heart valves detected by the mechanical sensor. Alternate types of non-electrical sensors would result in alternate types of signals. The detected acceleration signal 200, as shown in FIG. 5, has distinguishing features that separate different phases of the heart. The first peaks 202, 204 correspond to the closure of atrio-ventricular valves, the mitral valve closure 202 and the tricuspid valve closure 204, or the onset of systole, and the usually smaller, second peak 206 corresponds to the closure of semi-lunar valves, the aortic and pulmonary valve closures, or the onset of diastole.

Figure 6:
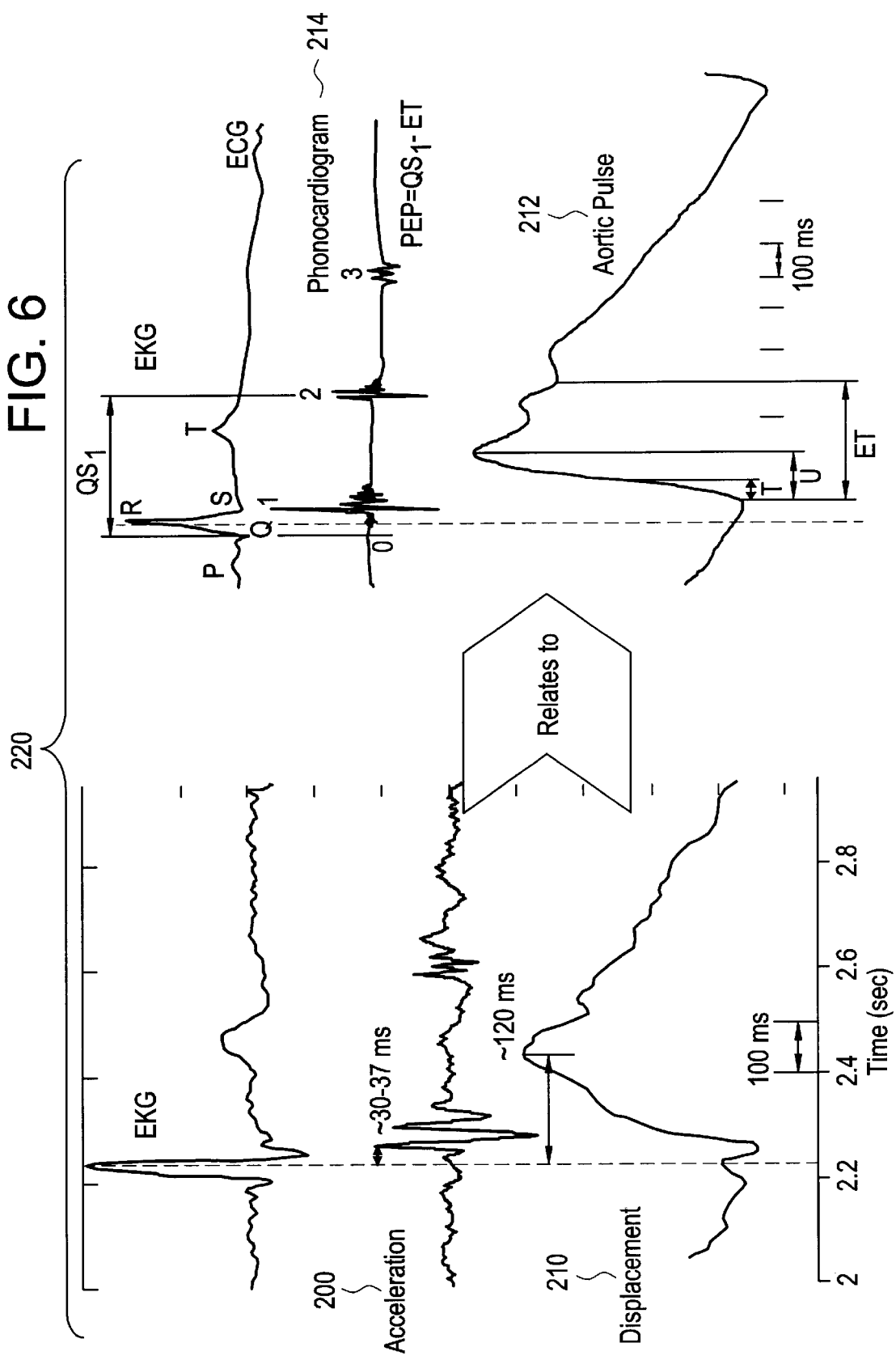
FIG. 6 shows a diagram of an acceleration signal, a blood pressure waveform, a phonocardiogram, and an aortic pulse signal.

As shown in FIG. 6, the blood pressure waveform 210 can be computationally derived from the acceleration waveform 200 by integrating the signal 200 twice over a given time interval and getting rid of the drift in the signal. The derived pressure waveform 210 correlates well with the aortic pulse 212 or the carotid pulse depending on the sensor location of the subject's body while the acceleration waveform 200 correlates well with the phonocardiogram 214, an acoustic signal that represents heart sounds. Alternatively, the acceleration signal 200 can be derived from the pressure waveform 210 by a second order derivative operation. The blood velocity factor (not shown) can be derived in the same way by either integrating the acceleration signal 200 over a given interval of time or by taking a first order derivative of the pressure waveform 210 and vice versa. Thus, cardiac information, shown in general at 220 extracted in one mode can be used to computationally derive information in the other mode without having to use multiple sensors.

Figure 1:
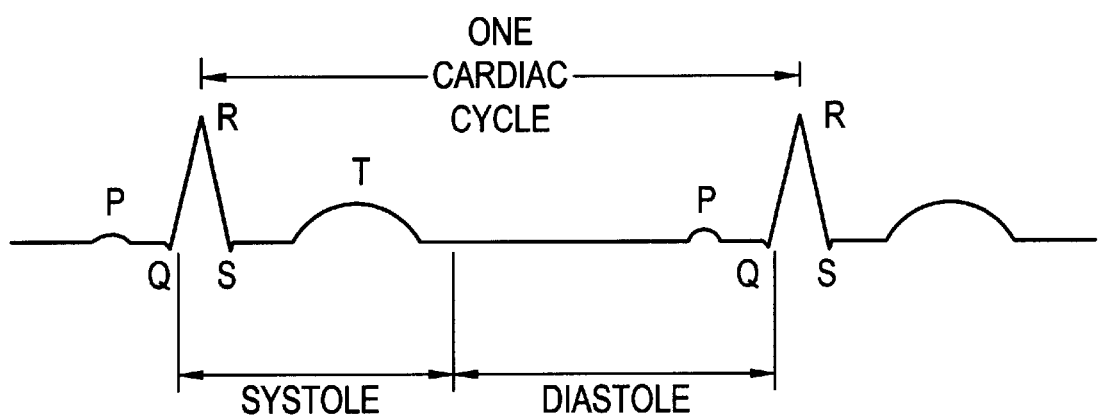
FIG. 1 shows a prior art EKG signal waveform used in known imaging systems.
Figure 2:
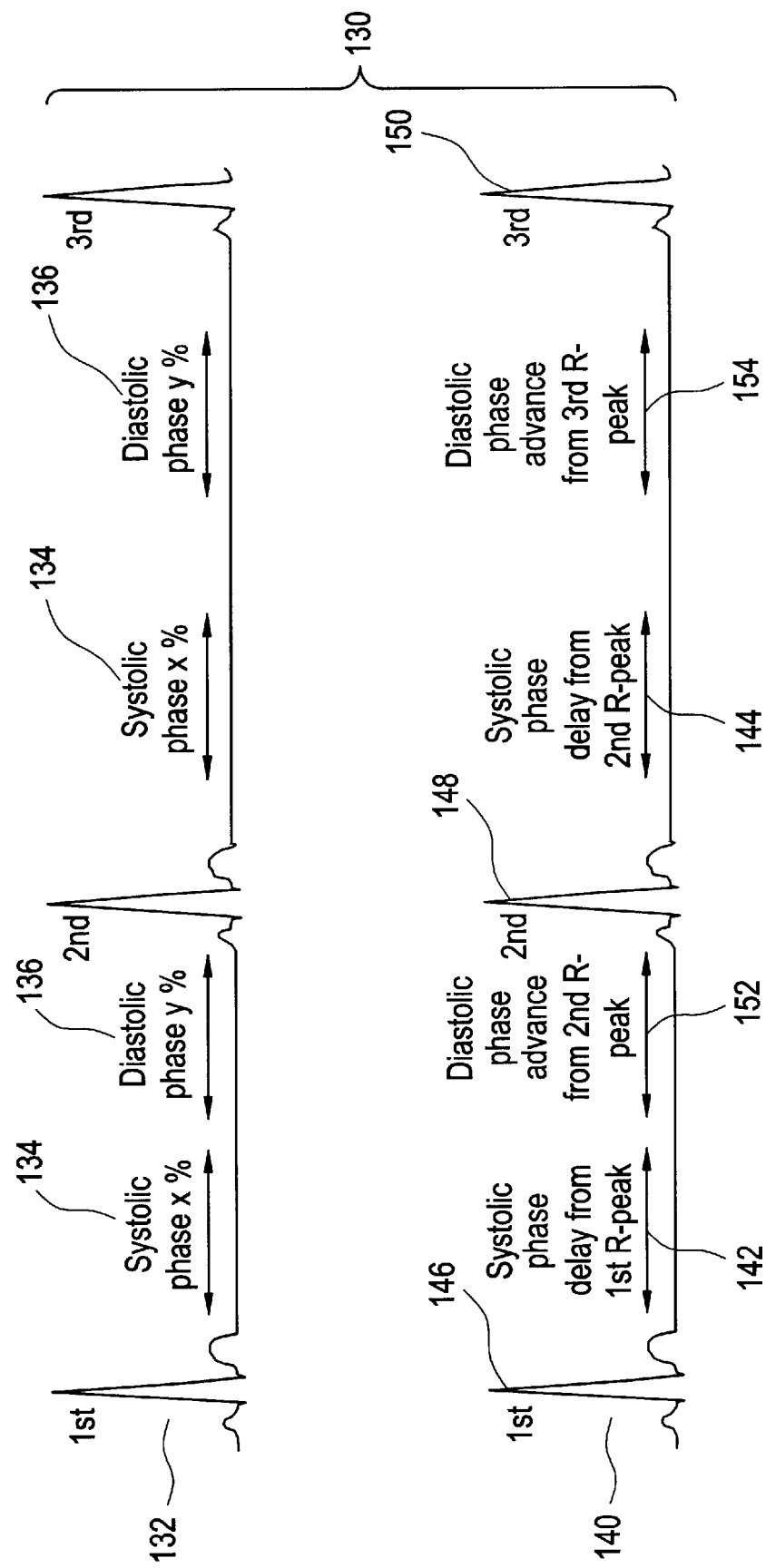
FIG. 2 shows prior art EKG waveforms where systolic and diastolic phases are estimated as centered within a particular percentage of the cardiac cycle or assumed to be a certain delay from an adjacent peak.
Figure 3:
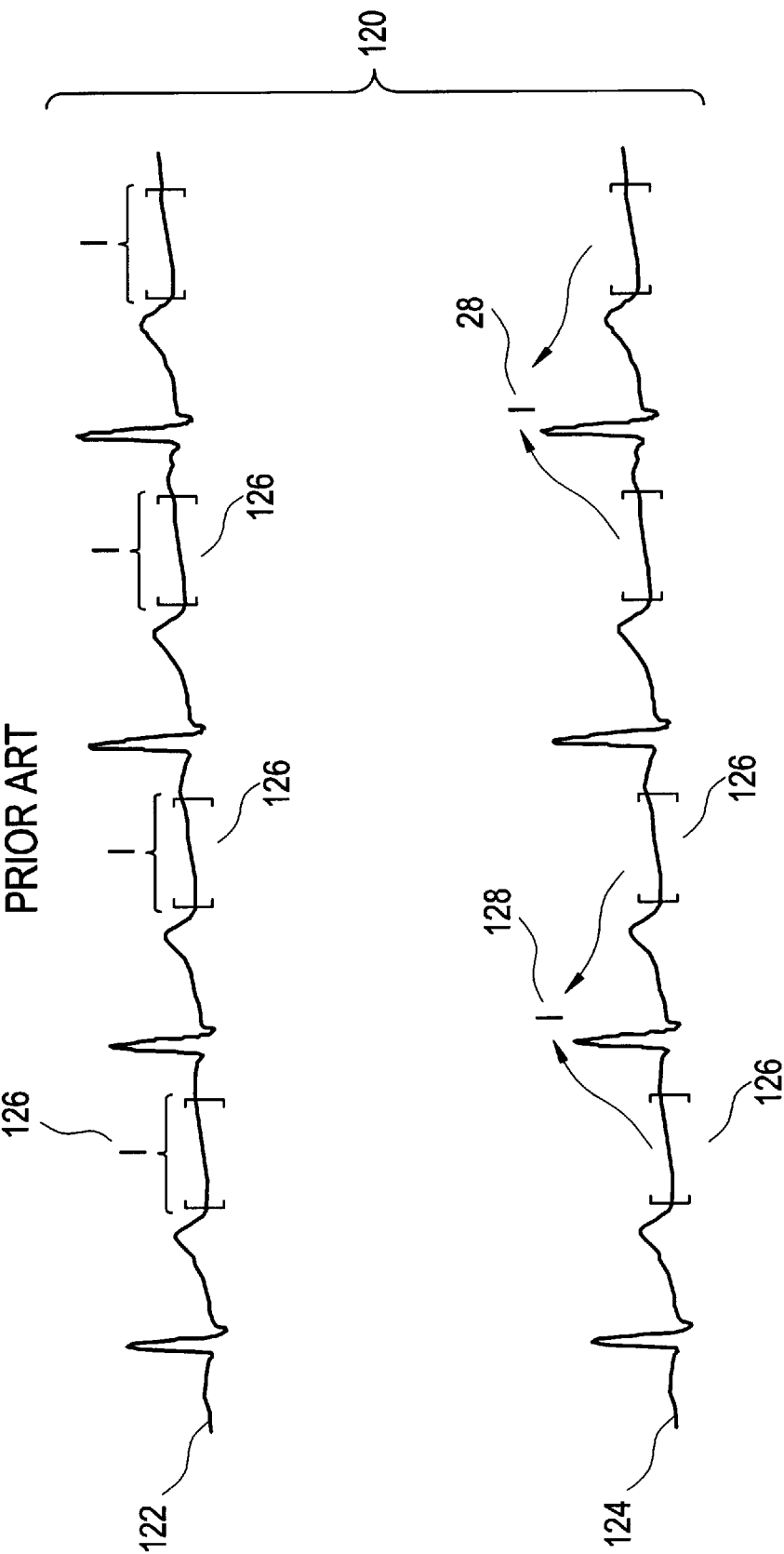
FIG. 3 shows prior art EKG waveforms where images are reconstructed from a single cycle or two consecutive cycles.
Figure 7:
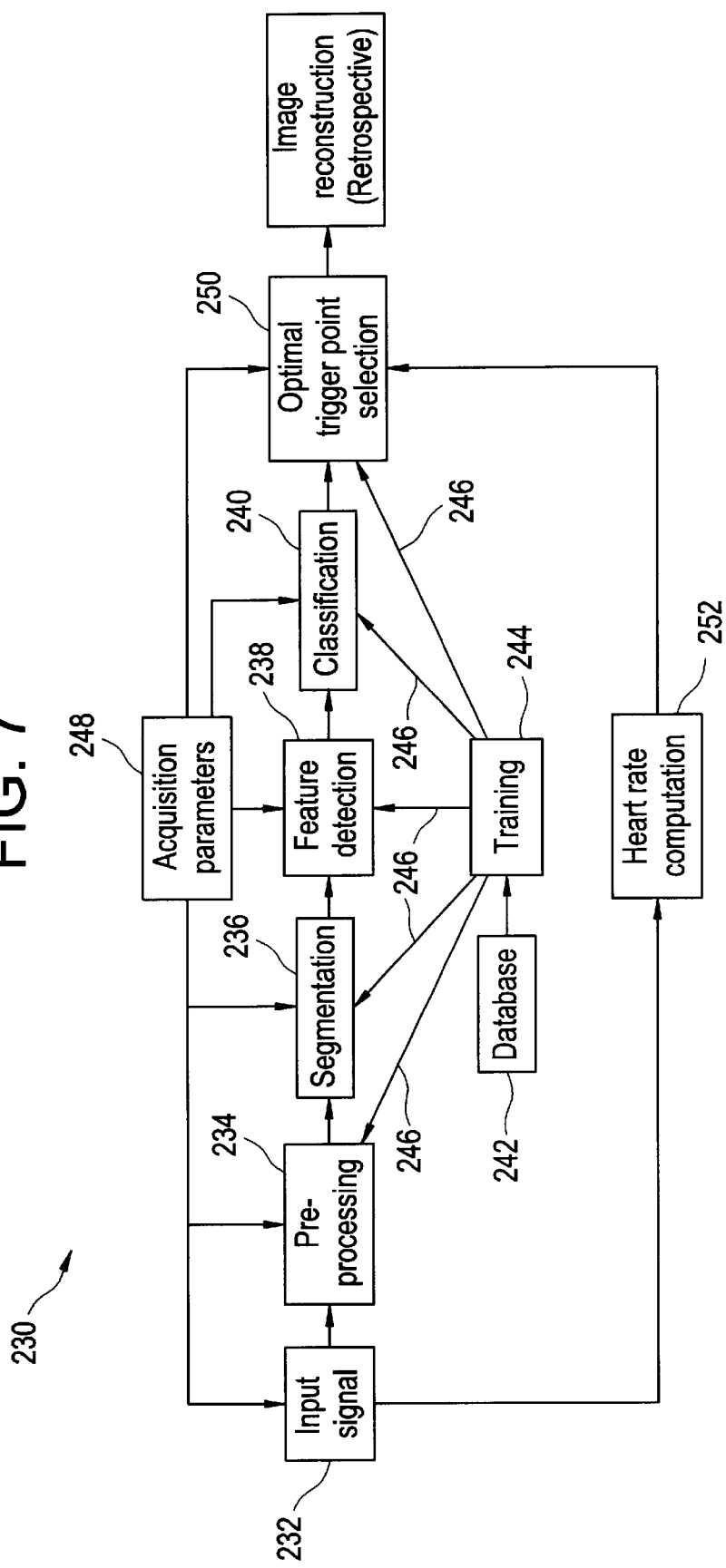
FIG. 7 shows a diagram of a trigger determination method.

In retrospective cardiac gating, trigger points need to be determined for each cardiac cycle and this information is then used for reconstructing images. As described with respect to FIGS. 2 and 3, the current approaches are not always accurate in determining phases. For determining optimal triggers in every cardiac cycle, the algorithm generalized in FIG. 7 is shown. FIG. 7 shows a diagram illustrating different processes in a trigger determination method, method, process, algorithm, and system 230. The segmentation block 236 may or may not be included in all trigger determination applications. The training process 244 here can use information from an existing database 242 to derive parameters in an unknown case. Individual modules in the trigger determination process 230 are further described below.

The Input signal 232 includes cardiac related data acquired from a non-electrical sensor, such as the mechanical sensor 12 described with respect to FIG. 4, although alternate arrangements and alternate non-electrical sensor assemblies for acquiring cardiac related data are also within the scope of this algorithm 230.

Regarding the Pre-processing 234, the principal objective of enhancement techniques is to process the data so that the result is more suitable than the original data for a specific application. The raw data can be pre-processed using spatial domain methods such as point processing methods including but not limited to exponentiation, spatial filtering methods including but not limited to various smoothing and sharpening operations, or frequency domain methods including various filters, or a combination of such methods.

Segmentation 236 subdivides a signal into its constituent parts, such as various phases or optimal trigger point selection based on pre-determined criteria. The level to which this subdivision is carried out depends on the problem being solved. This step 236 in the process 230 may determine the eventual success or failure of the analysis. In fact, effective segmentation rarely fails to lead to a successful solution. It should be noted here that segmentation 236 could be either performed before or after feature detection 238.

Regarding Feature Detection 238, signal analysis is a process of discovering, identifying and understanding patterns that are relevant to the performance of a signal-based task. Any signal analysis technique may include characteristics such as 1) ability to extract pertinent information from a background of irrelevant details; 2) capability to learn from examples and to generalize this knowledge so that it can apply to new and different circumstances; and 3) the ability to make inferences from incomplete information. Pattern recognition techniques such as template matching, neural networks, and structural methods, that use any structural relationship information in a pattern's shape, may be used to detect features in Feature Detection 238.

Once the features are computed in Feature Detection 238, a pre-trained classification algorithm in Classification 240 can be used to categorize the detected segments of the signal into different phases. Neural networks, rule-based methods or fuzzy logic can be used for classification, which are all well known in the art.

Figure 8:
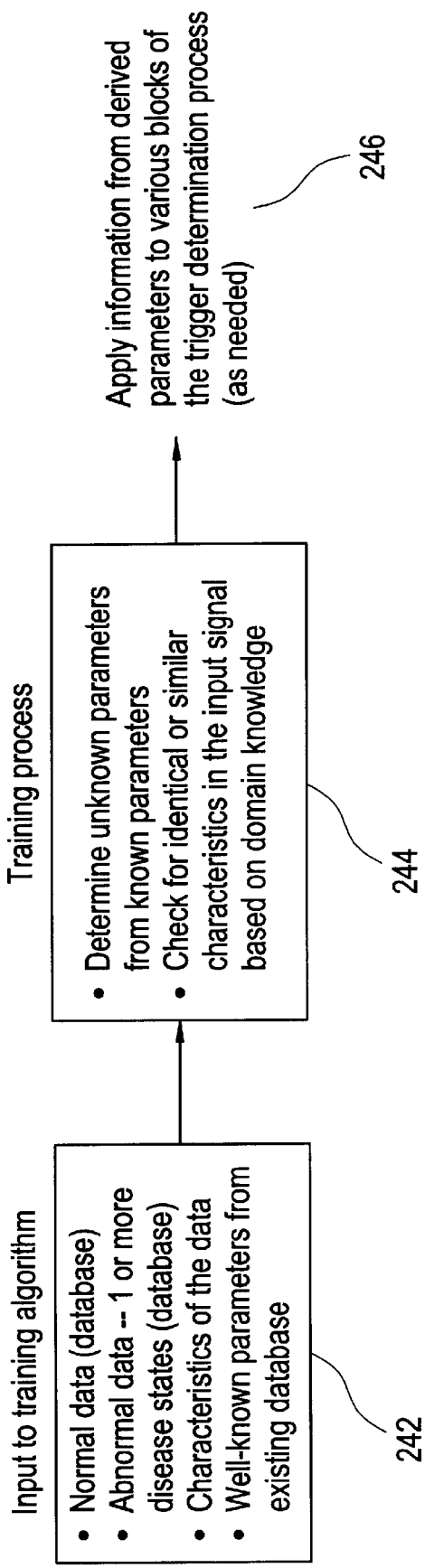
FIG. 8 shows a training process usable within the trigger determination method of FIG. 7.

A database 242 (raw cardiac data from a mechanical sensor) that includes both normal and abnormal (one or more disease states in each dataset) data is used for training the algorithm in training 244. As more specifically shown in FIG. 8 which shows a diagram of the training process, the training set 242 involves the computation of several candidate features such as characteristics of normal or abnormal (one or more disease states in each dataset) data, relationship between different disease states and specific signal characteristics and other pertinent factors from an existing database.

A feature selection algorithm, which may be performed subsequent to feature detection 238 or as part of classification 240, may sort through the candidate features and select only the useful ones and remove those that provide no information or redundant information. This decision may be based on classification results with different combinations of candidate features. The feature selection algorithm is also used to reduce the dimensionality from a practical standpoint since the computation time would be enormous if the number of features to compute is large. Thus, a feature set is derived that can optimally discriminate between the different features in a signal. Optimal feature selection can be performed using a well-known distance measure including divergence measure, Bhattacharya distance, Mahalanobis distance etc.

After the feature set is derived from the training process 244, suitable information is applied to the various blocks (e.g. Pre-processing 234, Segmentation 236, Feature detection 238, Classification 240, and Optimal trigger point selection 250) of the trigger determination process 230 as shown in FIG. 7.

Also shown in FIG. 7, Acquisition parameters 248 may be used in each step (e.g. Input signal 232, Pre-processing 234, Segmentation 236, Feature detection 238, Classification 240, and Optimal trigger point selection 250) of the process 230 to determine different criteria for optimal trigger selection 250. Acquisition parameters could be the sampling rate of the acquired signal, knowledge of the sensor location, type of signal being acquired, type of application, type of disease if already known, etc. Further, heart rate can be computed simultaneously via Heart rate computation 252 and fed into the final step of the process.

These basic processes, that is, the various blocks and steps shown in the overall method 230 can be done in parallel, or in various combinations. For a given application, only a few of these combinations may need to be used, but they are provided in all possibilities within FIG. 7 to indicate that several modifications of dataflow are possible.

Figure 9:
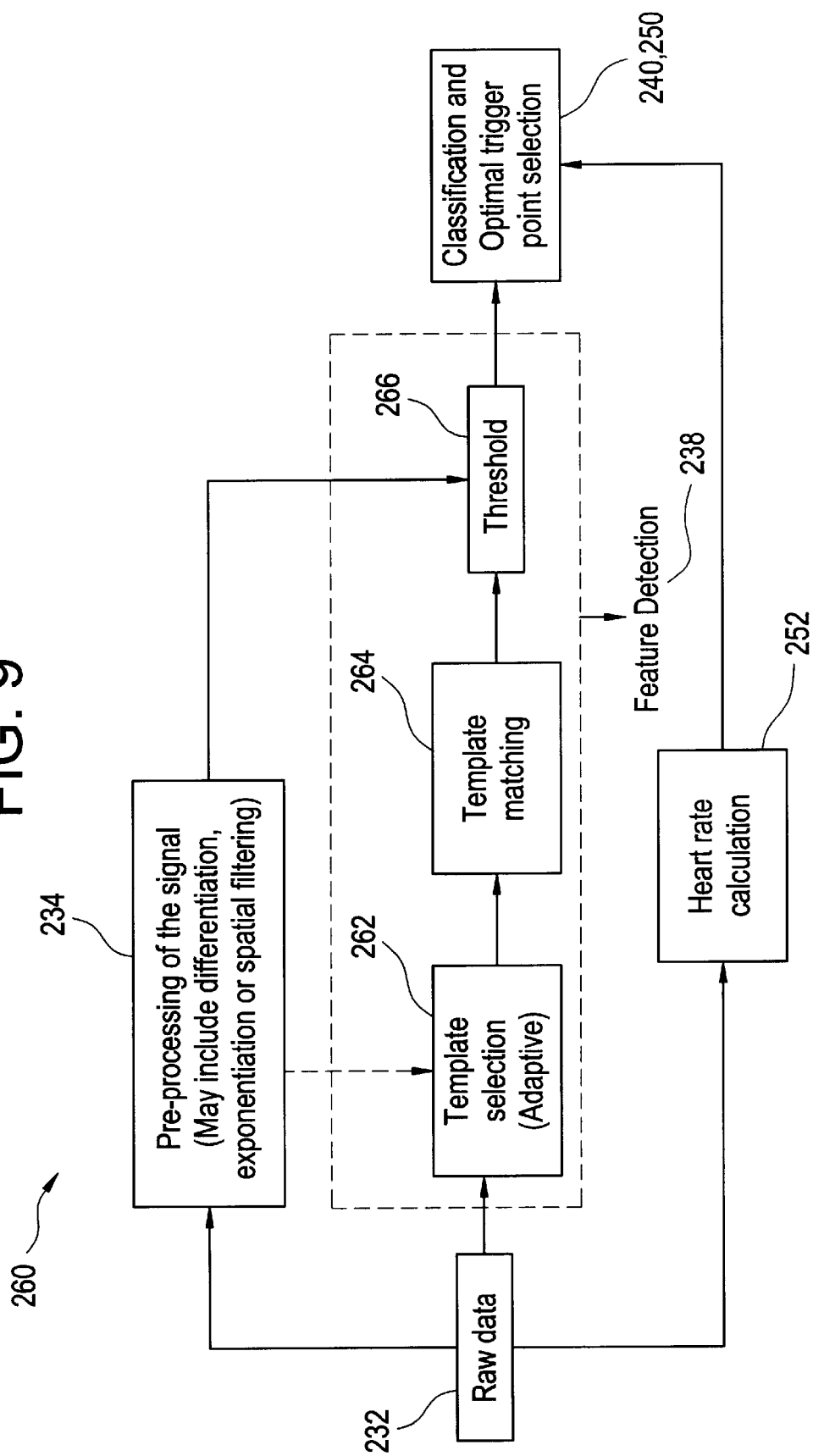
FIG. 9 shows a revised trigger determination method including a template matching method.

An example of one application of the framework for a process 230 is illustrated with a template matching method as shown in FIG. 9. An exemplary algorithm 260 for the pattern recognition approach is a revised version of the more general inclusive process 230. The algorithm 260 includes Input signal 232 and/or Pre-processing 234. The input signal 232 could be the raw data 232 or a pre-processed signal 234 depending on the feature that needs to be extracted. Alternatively, both the signals 232, 234 may be used in parallel.

Within Feature Detection 238, an automated, optimal template is selected from the first few seconds of each dataset that needs to be processed in Template Selection 262. Within Template matching 264, the selected template is matched against the real time signal to find a correlation vector.

The Threshold step 266 may include two separate processes. (1) Threshold the correlated vector from the Template matching step 264 to choose the points that are well correlated in each cardiac cycle. This process would identify a set of candidate trigger points in each cycle. Various criteria can be used to select the trigger points from this set. (2) Threshold the pre-processed signal 234 from the first step separately.

For Classification 240 one criterion is to use the data point with maximum correlation and not use any data points until the time corresponding to the current cardiac period is reached. Alternatively, the first data point exceeding the threshold after the current cardiac period can be used. Another method would involve using the segmented pre-processed signal along with the segmented correlation vector to determine an optimal trigger point 250 in each cycle. Optimal trigger point from Optimal Trigger point selection 250 for each cardiac cycle is sent to gate the imaging device.

An illustration of this approach is shown in FIG. 10 which diagrams template matching method applied on an acceleration signal 200. An optimal template 280 is selected from the first few seconds of data through template selection 262. Through template matching 264 and thresholding 266, candidate trigger points 282 are detected. Best trigger point selection 250 is shown using two different approaches. Trigger point 284 may be selected for exceeding a certain threshold, which may be pre-selected by a user/operator, and trigger point 286 may be selected for having maximum correlation, i.e. the best match of an acceleration signal with a template.

FIG. 11 shows the onset of systole 'S' and diastole 'D' phases. 'δ t' represents the time before the onset of different phases. 'T' represents the time interval (phase) the user would pick to reconstruct images at different phases and 'I' represents the images that are reconstructed. Once the trigger points are selected, e.g. 284 or 286 as shown in FIG. 10, a user can specify a time interval, δ t as illustrated in FIG. 11 within the waveforms 300, where he would want to reconstruct the images and the images could be reconstructed over an interval 'T'. This 'δ t' interval could be before the first peak of a cardiac cycle, e.g. 306, to capture atrial contraction, or before the second peak, e.g. 308, to capture the onset of diastole or at any arbitrary phase depending on the application. Images I are reconstructed for waveform 302 based on individual intervals T. This approach would also be of advantage in multi-section reconstruction, such as shown in waveform 304, where data from two or more cardiac cycles is used to reconstruct a single image I.

It should be understood that the above described methods are applicable to a variety of diagnostic modalities including, but not limited to, CT, MR, X-Ray, Ultrasound, and PET-CT.

Thus, the methods, processes, algorithm, and system disclosed herein provide the user with an ability to select different cardiac phases accurately based on the mechanical motion of the heart that was hitherto not possible. The framework described above provides the ability to determine cardiac phases based on mechanical motion of the heart and to determine different cardiac phases.

It should be noted that all of the methods described above may be employed within an imaging system or within a signal processor associated with a computer and display such as shown by item 50 in FIG. 5, and in particular, may be stored within a memory processed by a processing circuit in the processor. It is further within the scope of this invention that the disclosed methods may be embodied in the form of any computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method of selecting an optimal trigger point in a cardiac cycle, the method comprising:

providing an input signal including non-electrical cardiac related data;

analyzing the input signal to detect candidate features;

sorting through the candidate features to select optimal features; and, selecting an optimal trigger point.

2. The method of claim 1 further comprising pre-processing the input signal.

3. The method of claim 1 wherein providing the input signal includes both providing raw data and providing pre-processed data.

4. The method of claim 1 further comprising subdividing the input signal into parts.

5. The method of claim 1 further comprising a training process, wherein the training process provides information to at least one step within the method.

6. The method of claim 5 further comprising providing the training process with a training set of data.

7. The method of claim 6 further comprising providing the training set of data with characteristics of normal and abnormal data.

8. The method of claim 1 further comprising categorizing the optimal features prior to selecting an optimal trigger point.

9. The method of claim 1 further comprising applying acquisition parameters to at least one step within the method.

10. The method of claim 1 further comprising using the input signal to compute heart rate.

11. The method of claim 10 further comprising using the heart rate in selecting an optimal trigger point.

12. The method of claim 1 wherein analyzing the input signal to detect candidate features comprises selecting an optimal template from a first few seconds of a dataset for processing.

13. The method of claim 12 further comprising comparing the optimal template to the input signal for finding a correlation vector.

14. The method of claim 13 further comprising thresholding the correlated vector for choosing correlated points in a cardiac cycle, wherein the correlated points identify a set of candidate trigger points.

15. The method of claim 14 further comprising selecting a trigger point with maximum correlation as the optimal trigger point.

16. The method of claim 14 further comprising selecting a trigger point which exceeds a threshold prior to other trigger points as the optimal trigger point.

17. The method of claim 1 further comprising obtaining the input signals from a mechanical sensor.

18. A method of selecting an arbitrary cardiac phase using non-electrical signals for cardiac gating, the method-comprising:
   identifying a trigger point identifying onset of a systole or diastole phase on a signal, the trigger point existing at time t1;
   specifying a time δ t before the trigger point and extending from a time t0 to a time t1, wherein time t0 is earlier than time t1; and,
   selecting a time interval T over which an image will be reconstructed, wherein
      the time interval T extends from time t0 to a time t2, wherein time t2 is later than time t0.

19. The method of claim 18 wherein time t2 is later than time t1.

20. The method of claim 18 wherein the signal is an acceleration signal.

21. The method of claim 18 wherein identifying a trigger point comprises:
   providing an input signal including non-electrical cardiac related data;
   analyzing the input signal to detect candidate features;
   sorting through the candidate features to select optimal features; and, selecting an optimal trigger point.

22. The method of claim 21 wherein analyzing the input signal to detect candidate features comprises selecting an optimal template from a first few seconds of a dataset for processing.

23. The method of claim 22 further comprising comparing the optimal template to the input signal for finding a correlation vector.

24. The method of claim 23 further comprising thresholding the correlated vector for choosing correlated points in a cardiac cycle, wherein the correlated points identify a set of candidate trigger points.

25. The method of claim 24 further comprising selecting a trigger point with maximum correlation as the optimal trigger point.

26. The method of claim 24 further comprising selecting a trigger point which exceeds a preselected threshold prior to other trigger points as the optimal trigger point.

27. The method of claim 18 wherein specifying a time δ t comprises a user selecting a time δ t.

28. A method of image reconstruction using cardiac gating, the method comprising:
   providing a non-electrical signal indicative of a plurality of consecutive cardiac cycles, for each cardiac cycle, the method further comprising:
      identifying a trigger point identifying onset of a systole or diastole phase, the trigger point existing at time t1;
      specifying a time δ t before the trigger point and extending from a time t0 to a time t1, wherein time t0 is earlier than time t1;
      selecting a time interval T over which an image will be reconstructed, wherein
         the time interval T extends from time t0 to a time t2, wherein time t2 is later than time t0; and,
      reconstructing an image over at least one time interval T.

29. The method of claim 28 wherein reconstructing an image over at least one time interval T comprises reconstructing an image over two adjacent time intervals T.

30. A storage medium encoded with a machine readable computer program code, said code including instructions for causing a computer to implement a method for selecting an optimal trigger point in a cardiac cycle, the method comprising:
   providing an input signal including non-electrical cardiac related data;
   analyzing the input signal to detect candidate features;
   sorting through the candidate features to select optimal features; and,
   selecting an optimal trigger point.

31. A storage medium encoded with a machine readable computer program code, said code including instructions for causing a computer to implement a method for selecting an arbitrary cardiac phase for cardiac gating, the method comprising:
   identifying a trigger point identifying onset of a systole or diastole phase on a signal, the trigger point existing at time t1;
   specifying a time δ t before the trigger point and extending from a time t0 to a time t1, wherein time t0 is earlier than time t1; and
   selecting a time interval T over which an image will be reconstructed, wherein
      the time interval T extends from time t0 to a time t2, wherein time t2 is later than time t0.

32. A system for selecting an optimal trigger point in a cardiac cycle, the system comprising:
   a non-electrical sensor sensing mechanical vibrations of the heart;
   a processing circuit coupled to the mechanical sensor, the processing circuit processing a signal sent by the mechanical sensor, analyzing the signal to detect candidate features, sorting through the candidate features to select optimal features, and selecting an optimal trigger point.

33. A system for image reconstruction using cardiac gating, the system comprising:
- a non-electrical sensor sensing mechanical vibrations of the heart;
- a processing circuit coupled to the mechanical sensor, the processing circuit processing a signal sent by the mechanical sensor, identifying a trigger point identifying onset of a systole or diastole phase on the signal, the trigger point existing at time t1, specifying a time $\delta t$ before the trigger point and extending from a time t0 to a time t1, wherein time t0 is earlier than time t1, and selecting a time interval T over which an image will be reconstructed, wherein the time interval T extends from time t0 to a time t2, wherein time t2 is later than time t0.

* * * * *

UNITED STATES PATENT AND TRADEMARK OFFICE
CERTIFICATE OF CORRECTION

PATENT NO. : 6,771,999 B2
APPLICATION NO. : 10/065961
DATED : August 3, 2004
INVENTOR(S) : Prathyusha K. Salla et al.

It is certified that error appears in the above-identified patent and that said Letters Patent is hereby corrected as shown below:

Title page,
Item (57) Abstract, after "time" (second occurrence), delete "δ t" and insert therefor --δt --.

Column 2,
Line 42, after "time" (first occurrence), delete "δ t" and insert therefor --δt --.
Line 52, after "time" (second occurrence), delete "δ t" and insert therefor --δt --.

Column 3,
Line 7, after "time" (second occurrence), delete "δ t" and insert therefor --δt --.
Line 28, after "time", delete "δ" and insert therefor --δt --.

Column 7,
Line 46, after "phases.", delete "'δ t'" and insert therefor --'δt' --.
Line 51, after "interval," delete "δ t" and insert there for --δt --.
Line 54, after "This", delete "'δ t'" and insert therefor --'δt' --.

Column 9,
Line 43, after "time", delete "δ t" and insert therefor --δt --.

Column 10,
Line 11, after "time", delete "δ t" and insert therefor --δt --.
Line 20, after "time", delete "δ t" and insert therefor --δt --.
Line 51, after "time", delete "δ t" and insert therefor --δt --.

UNITED STATES PATENT AND TRADEMARK OFFICE
CERTIFICATE OF CORRECTION

PATENT NO. : 6,771,999 B2
APPLICATION NO. : 10/065961
DATED : August 3, 2004
INVENTOR(S) : Prathyusha K. Salla et al.

It is certified that error appears in the above-identified patent and that said Letters Patent is hereby corrected as shown below:

Column 11,
Line 9, after "time" (second occurrence), delete "$\delta$ t" and insert therefor --$\delta t$--.

Signed and Sealed this

Eighth Day of August, 2006

JON W. DUDAS
*Director of the United States Patent and Trademark Office*